United States Patent [19]

McShane

[11] Patent Number: 4,775,751
[45] Date of Patent: Oct. 4, 1988

[54] PROCESS FOR CEPHALEXIN HYDROCHLORIDE ALCOHOLATES

[75] Inventor: Lawrence J. McShane, Indianapolis, Ind.

[73] Assignee: Eli Lilly & Company, Indianapolis, Ind.

[21] Appl. No.: 740,720

[22] Filed: Jun. 3, 1985

[51] Int. Cl.[4] ................ C07D 501/22; A61K 31/545
[52] U.S. Cl. .................................... 540/230; 540/228; 540/220
[58] Field of Search ....................... 540/230, 228, 220

[56] References Cited

U.S. PATENT DOCUMENTS

| | | | |
|---|---|---|---|
| 3,507,861 | 4/1970 | Morin et al. | 260/243 |
| 3,531,481 | 9/1970 | Pfeiffer | 260/243 |
| 3,655,656 | 4/1972 | Heyningen | 260/243 C |
| 3,781,282 | 12/1973 | Garbrecht | 260/243 C |
| 4,600,773 | 7/1986 | Engel et al. | 544/30 |

FOREIGN PATENT DOCUMENTS 901142  5/1985  Belgium .
50-151890  6/1975  Japan .

OTHER PUBLICATIONS

Pfeiffer, Yang, Tucker, *Journal of Pharmaceutical Sciences*, vol. 59, No. 12, Dec. 1970, "Crystal Pseudopolymorphism of Cephaloglycin and Cephalexin".

*Primary Examiner*—Nicholas S. Rizzo

[57] ABSTRACT

The crystalline ethanol or methanol solvates of cephalexin hydrochloride are isolated in high yield from solutions of cephalexin hydrochloride in substantially anhydrous ethanol or methanol, respectively, by adding miscible $C_5$–$C_6$ alkanes after initiating solvate crystallization. Ethanol or methanol solutions of cephalexin hydrochloride can be prepared by adding gaseous HCl to the respective alcohol slurries of cephalexin monohydrate or the novel crystalline ethanolate or desolvated ethanolate. Alternatively, the cephalexin bis-DMF solvate-derived cephalexin hydrochloride isopropanolate can be used to prepare the crystalline hydrochloride monohydrate in accordance with the disclosed improved method.

27 Claims, No Drawings

PROCESS FOR CEPHALEXIN HYDROCHLORIDE ALCOHOLATES

BACKGROUND OF THE INVENTION

This invention relates to cephalosporin antibiotics and, in particular, to processes for the preparation of crystalline cephalexin intermediates useful for the production of cephalexin hydrochloride monohydrate.

Cephalexin is the generic term used to identify the chemical compound 7-(D-2-amino-2-phenylacetamido-3-methyl-3-cephem-4-carboxylic acid. That compound is described in U.S. Pat. No. 3,507,861. Later patents including U.S. Pat. Nos. 3,655,656 and 3,781,282 have described processes for preparing unique forms of cephalexin. The '656 patent describes a process for preparing cephalexin monohydrate which is a highly crystalline dense form of cephalexin ideally suited to formulation into capsules and tablets for human therapy. U.S. Pat. No. 3,781,282 describes and claims cephalexin bis(N,N-dimethylformamide) solvate, a valuable crystalline intermediate for the production of cephalexin and cephalexin derivatives.

While cephalexin monohydrate has enjoyed widespread commercial success as a 2-4 times a day treatment for bacterial infections, that form of cephalexin has relatively low water solubility. The relatively low water solubility of cephalexin monohydrate may, in some instances, delay its absorption so that the high blood levels achievable with cephalexin are not immediately realized following administration of conventional cephalexin monohydrate formulations.

Recently it has been found that crystalline cephalexin hydrochloride monohydrate exhibits much improved solubility characteristics over that of cephalexin monohydrate. That particular crystalline form of cephalexin, cephalexin hydrochloride monohydrate, is prepared by exposing crystalline cephalexin hydrochloride ethanol solvate (ethanolate) to an atmosphere having a relative humidity of about 10 to about 50 percent. The ethanol solvate intermediate used to prepare the more soluble cephalexin hydrochloride monohydrate is obtained from ethanol solutions of cephalexin hydrochloride formed by treating suspensions of cephalexin monohydrate in ethanol with gaseous hydrogen chloride.

An object of this invention is to provide an improved method for the preparation of crystalline cephalexin hydrochloride $C_1$-$C_2$ alkanolates, useful intermediates for the production of crystalline cephalexin hydrochloride monohydrate.

A further object is to provide a high yielding method for preparation of cephalexin hydrochloride isopropanolate from the art-recognized cephalexin bis-dimethylformamide solvate.

Another object of this invention is to provide a method for preparing two crystalline forms of cephalexin, novel cephalexin ethanolate and desolvated cephalexin ethaholate, from cephalexin bis-dimethylformamide solvate. Those crystalline forms of cephalexin can be used as starting materials in the present improved method for the preparation of cephalexin hydrochloride alcoholates.

SUMMARY OF THE INVENTION

This invention concerns an improved, high yielding method for the preparation of crystalline cephalexin hydrochloride $C_1$-$C_2$ alkanol solvates which can be converted to crystalline cephalexin hydrochloride monohydrate directly by exposure to an atmosphere having a relative humidity of about 10 to about 50 percent. Yields of crystalline cephalexin hydrochloride alkanol solvates are increased dramatically by the addition of alcohol miscible lower alkanes selected from $C_5$-$C_6$ alkanes and $C_5$-$C_6$ cycloalkanes to crystal-forming alkanol solution of cephalexin hydrochloride. Because the radical differences in polarity of the $C_1$-$C_3$ alcohols from which cephalexin solvates have been crystallized in the past, and the presently employed lower alkane "anti-solvents," it was not expected that such anti-solvents could be used effectively to increase the yield of crystalline cephalexin hydrochloride alcohol solvates.

In another embodiment of this invention crystalline cephalexin hydrochloride isopropanolate is separated from a crystallizing medium formed by adding concentrated hydrochloric acid to a slurry of the bis-DMF solvate of cephalexin in isopropanol. The crystalline cephalexin hydrochloride isopropanolate can be used as an intermediate for preparation of the corresponding ethanol solvate via the improved process embodiment of this invention.

Still another embodiment is the preparation of crystalline cephalexin ethanolate by treatment of the corresponding bis-DMF solvate with substantially anhydrous ethanol. The novel crystalline cephalexin ethanolate the and crystalline desolvated cephalexin ethanolate can be used as starting materials in the present improved process for crystalline cephalexin hydrochloride ethanolate or methanolate, each of which can be converted to the water soluble cephalexin hydrochloride monohydrate by exposure to humid air.

DETAILED DESCRIPTION OF THE INVENTION

Cephalexin hydrochloride ethanol solvate (ethanolate) is a known crystalline form of cephalexin. It like the corresponding methanol solvate (methanolate) is a stable crystalline material in the absence of moisture. However, when exposed to ambient air or artificially humidified air having a relative humidity of about 10 to about 50 percent, those crystalline materials are converted by such "humidification" process to the corresponding crystalline cephalexin hydrochloride monohydrate. The reaction appears to be an actual crystal transformation from crystalline ethanolate or methanolate to crystalline monohydrate.

Crystalline cephalexin hydrochloride ethanolate has been prepared by forming a solution of cephalexin hydrochloride in ethanol by adding gaseous HCl to an ethanolic suspension of cephalexin monohydrate. Crystalline cephalexin hydrochloride ethanolate precipitates from the ethanol solution in yields typically ranging from 40-60 percent.

One aspect of this invention is directed to an improved method for the preparation of crystalline cephalexin hydrochloride ethanolate and cephalexin hydrochloride methanolate. The present improved method comprises forming a solution of cephalexin hydrochloride in a volume of substantially anhydrous ethanol or methanol respectively, initiating crystallization of the solvate if necessary, and then adding up to an equivalent volume of an alcohol miscible lower alkane selected from $C_5$-$C_6$ alkanes and $C_5$-$C_6$ cycloalkanes to form a crystal-forming medium from which can be separated the crystalline cephalexin hydrochloride solvate in yields ranging from about 85 to 95 percent. The present improved method achieves a significant increase in yield over that which has been used previously to prepare crystalline cephalexin hydrochloride ethanolate. While the use of so-called "anti-solvents" for compound crystallizations is recognized in the art, it is unusual and unexpected that such high yields of crystalline cephalexin hydrochloride solvates are obtained by the addition of alkanes to the respective alcoholic solutions thereof. Given the radical differences in polarity and product solubility in methanol/ethanol and $C_5$-$C_6$ alkanes the skilled practitioner would have predicted precipitation of amorphous material as opposed to the highly crystalline product obtained in accordance with the present improved method.

The first step in carrying out the present improved method for preparing cephalexin hydrochloride methanolate or ethanolate is the formation of a solution of cephalexin hydrochloride in a volume of substantially anhydrous ethanol or methanol, respectively. The alcohol used determines the nature of the alcohol solvate in the crystalline product. The term "substantially anhydrous" as applied here to the ethanol or methanol used to form the solution of cephalexin hydrochloride means that water in the ethanol/methanol should be kept to a minimum. Highest product yields are obtained with the dryest alcohols. It is preferred that the alcohol used in the present improved process contains not more than 1.0 percent water, more preferably not more than 0.2 percent and most preferably not more than 0.05 percent water, as determined by the Karl Fischer method of analysis.

The alcohol (ethanol or methanol) solution of cephalexin hydrochloride can be formed by adding cephalexin hydrochloride itself, or a solvated form thereof, to the substantially anhydrous alcohol, or the cephalexin hydrochloride can be formed in situ by the addition of at least a molar equivalent amount of gaseous HCl to a suspension or solution of cephalexin in the form of its zwitterion or a complex thereof in substantially anhydrous ethanol or methanol. Thus, the solution of cephalexin hydrochloride can be formed by dissolving, for example, cephalexin hydrochloride isopropanolate in substantially anhydrous ethanol or methanol or by adding gaseous HCl, preferably about 1 to about 4 molar equivalents, to a solution or suspension of, for example, cephalexin monohydrate, cephalexin ethanolate, or cephalexin anhydrate. Regardless of how the solution is formed it is preferred for maximum yields that the concentration of cephalexin hydrochloride be between about 0.2 and about 1.0 grams of cephalexin hydrochloride per milliliter of methanol or ethanol. Within that concentration range the cephalexin hydrochloride solvate typically begins to crystallize spontaneously from the alcohol solution. If crystallization is not spontaneous, that is, if no crystal formation can be detected after stirring for about ½ hour at room temperature, crystallization of the cephalexin hydrochloride solvate can be initiated by seeding the mixture with a few milligrams of the respective crystalline cephalexin hydrochloride solvate or the derived crystalline cephalexin hydrochloride monohydrate.

The yield of crystalline cephalexin hydrochloride ethanolate or methanolate is dramatically enhanced in accordance with the improved method of this invention by adding to the ethanolic or methanolic solution of cephalexin hydrochloride up to an equivalent volume of an alcohol miscible lower alkane selected from $C_5$-$C_6$ alkanes and $C_5$-$C_6$ cycloalkanes to form a crystal-forming medium. Exemplary of lower alkanes which can be employed in this process are hexane, cyclohexane, pentane, cyclopentane, low boiling petroleum ether, and mixtures of isomeric hexanes or pentanes available from most chemical suppliers. One such product which can be employed economically in the present process is a product labeled "Hexanes" sold by Mallinckrodt. The product is a mixture of isomeric hexanes boiling within a range of 68.5° C. to 69.2° C. The exact composition of the lower alkane employed in the present process is not critical so long as the alkane or alkane mixture is substantially miscible with the ethanolic or methanolic solution of cephalexin hydrochloride over the volume ratios defined herein.

While the addition of even small amounts of a lower alkane to the crystal-forming medium will increase the yield of the respective crystalline cephalexin hydrochloride solvate, it is preferred, to achieve the improved crystalline product yields in accordance with this process, that the amount of alkane added to the ethanolic or methanolic solution is about 20 to about 50 percent, and most preferably about 40 percent, of the total volume of the crystal-forming medium.

Following the alkane addition to the solvate crystallization mixture, it is preferred that the resulting crystal-forming medium be stirred for a period of time ranging from about 15 minutes to about two hours prior to separating the product crystalline solvate from the crystal-forming medium. Optionally the temperature of the crystal slurry can be lowered to between about 0° and about 15° C. to enhance crystal formation.

The product crystalline cephalexin hydrochloride solvate (methanolate or ethanolate) is easily separated from the crystal-forming medium by vacuum filtration. The crystalline solvates prepared in accordance with the above description are stable when bottled in an air-tight container. Typically, however, the solvate is "dried" at ambient temperature and humidity, during which process (actually a humidification process), the alcohol solvate converts to the crystalline cephalexin hydrochloride monohydrate. The crystalline cephalexin hydrochloride methanolate appears to undergo that "humidification" reaction at a faster rate than the corresponding ethanolate.

Assay adjusted yields of crystalline cephalexin hydrochloride solvate (methanolate or ethanolate) and, thus the derived cephalexin hydrochloride monohydrate, range from about 85 to about 95 percent. These yields evidence a significant improvement over the yields available in accordance with the art-recognized process.

For reasons not completely understood attempts to prepare crystalline cephalexin hydrochloride ethanolate and cephalexin hydrochloride methanolate directly from cephalexin bis-DMF solvate in accordance with the aforedescribed method has met with little success. That chemical conversion (bis-DMF solvate to ethanolate or methanolate) has been accomplished only by an indirect route involving conversion of the bis-DMF solvate to the intermediate cephalexin hydrochloride isopropanolate or to a novel crystalline cephalexin ethanolate and desolvated cephalexin ethanolate in accordance with further embodiments of the present invention described below.

Cephalexin bis-DMF solvate can be converted into crystalline cephalexin ethanolate which dries in air to crystalline desolvated cephalexin ethanolate. Either of those products, cephalexin ethanolate or desolvated cephalexin ethanolate, can be used as a source of cephalexin for the preparation of solutions of cephalexin hydrochloride in accordance with the improved method described hereinabove. The conversion of cephalexin bis-DMF solvate to the ethanolate can be effected by stirring a slurry of the DMF solvate in substantially anhydrous ethanol at room temperature for a period of time ranging from about one hour to about 24 hours. Apparently crystalline cephalexin ethanolate is less soluble in substantially anhydrous ethanol than is the starting cephalexin bis-DMF solvate. In other words, the bis-DMF solvate gradually dissolves in ethanol as the cephalexin ethanolate crystallizes from solution. The reaction begins as a slurry of the bis-DMF solvate in ethanol and progresses through gradual dissolving of the bis-DMF solvate and crystallization of the less soluble cephalexin ethanolate. Following completion of the reaction, a novel crystalline form of cephalexin, cephalexin ethanolate, can be filtered from the reaction medium. A nuclear magnetic resonance spectrum of the crystalline product obtained by filtering the reaction mixture after stirring six hours at room temperature shows less than 10 mole percent of DMF present in the crystalline product. The mole percent of DMF, i.e. the amount of unconverted starting material (the bis-DMF solvate) still present in the slurry, is decreased with longer reaction times.

Like the cephalexin hydrochloride ethanolate, the present crystalline cephalexin ethanolate is stable when kept in an air-tight container but unstable when exposed to ambient air. However, unlike crystalline cephalexin hydrochloride ethanolate which "humidifies" to the corresponding monohydrate, crystalline cephalexin ethanolate gives up the ethanol solvate molecule to form a crystalline desolvated cephalexin ethanolate which is stable at low humidity.

Either cephalexin ethanolate or desolvated cephalexin ethanolate can be used to prepare solutions of cephalexin hydrochloride for the preparation of cephalexin hydrochloride ethanolate or methanolate in accordance with the above-described improved method of the present invention. Because of the above-discussed tendency of cephalexin ethanolate to "give up" ethanol solvate molecules when exposed to air, it is preferred that when cephalexin ethanolate is to be used as a starting material, for example, for the preparation of cephalexin hydrochloride alcoholates, it is used as the ethanol solvate wet cake obtained by filtration of that product from ethanol.

In the above description of the improved process embodiment of this invention it was noted that solutions of cephalexin hydrochloride in ethanol can be prepared by dissolving cephalexin hydrochloride isopropanolate, a known crystalline solvate derivative of cephalexin, in ethanol or methanol. Cephalexin hydrochloride isopropanolate has been prepared in low yield by treating suspensions of cephalexin monohydrate in isopropyl alcohol with gaseous hydrogen chloride. Yields for that conversion of cephalexin monohydrate to cephalexin hydrochloride isopropanolate are low. Considering that and the fact that cephalexin monohydrate is itself the form of the currently marketed antibiotic and further that it can be converted directly in accordance with the improved process of this invention to cephalexin hydrochloride ethanolate and the corresponding monohydrate, the isopropanolate solvate of cephalexin hydrochloride has been viewed more as a curiosity than a viable commercial intermediate. Attempts to prepare the cephalexin hydrochloride isopropanolate from cephalexin bis-DMF solvate, a commonly available intermediate, by using gaseous HCl in isopropanol have been unsuccessful. It has been found that cephalexin bis-DMF solvate can be converted in high yield to crystalline cephalexin hydrochloride isopropanolate by adding at least one molar equivalent of concentrated hydrochloric acid (as opposed to gaseous HCl) to a suspension of cephalexin bis-DMF solvate in isopropyl alcohol. The water added to the reaction mixture by virtue of using concentrated hydrochloric acid as opposed to gaseous HCl appears necessary to the formation of crystalline cephalexin hydrochloride isopropanolate.

The preparation of cephalexin hydrochloride isopropanolate from the bis-DMF solvate can be conducted over a wide range of concentrations in isopropanol. Preferably about 5 to about 15 milliliters of isopropanol is employed for each gram of cephalexin bis-DMF solvate. Best results have been obtained when about 10 milliliters of isopropanol is used for each gram of cephalexin bis-DMF solvate. Preferably a slurry of cephalexin bis-DMF solvate in isopropyl alcohol is cooled to between about 10° and about 20° C. prior to the dropwise addition of concentrated hydrochloric acid. The addition of hydrochloric acid is usually accompanied by an increase in temperature of the reaction mixture. Best results are obtained when an excess of concentrated HCl is added to the bis-DMF solvate slurry. A 1.5 to 5.0-fold molar excess is preferred; a 3.0 to 4.0-fold molar excess of concentrated HCl is most preferred.

The crystalline product, cephalexin hydrochloride isopropanolate, appears in the reaction mixture as an almost granular crystalline material. Preferably crystallization can be initiated by the addition of a few milligrams of crystals of cephalexin hydrochloride isopropanolate. Once crystallization is initiated in the reaction mixture, yields of the product can be increased (as in the improved process for preparing cephalexin hydrochloride ethanolate and methanolate in accordance with the above described improved process of the present invention) by adding a volume of $C_5$–$C_6$ alkanes or $C_5$–$C_6$ cycloalkanes to the crystal-forming medium. The volume of said added alkanes preferably equals about 20 to about 50 percent of the total volume of the crystal-forming medium.

The present process for the preparation of cephalexin hydrochloride isopropanolate can be performed successfully even with very poor quality starting material. Thus, the process can be used advantageously to retrieve cephalexin values in high yield from poor quality cephalexin-containing compositions.

The practice of the present invention is further illustrated by the following detailed examples, none of which are to be construed as limiting the invention in any respect. In the following examples HPLC is high performance liquid chromatography; NMR is nuclear magnetic resonance spectrum; $DMSOd_6$ is deuterated dimethylsulfoxide; $D_2O$ is deuterated water; K.F. refers to percentage water determined by the Karl Fischer method of analysis; DMF is dimethylformamide; and "hexanes" refers to a product distributed by Mallinckrodt containing isomeric hexanes boiling in the range of 68.5° C. to 69.2° C.

PREPARATION 1

Cephalexin Bis-Dimethylformamide Solvate

A mixture of 26.0 g of p-toluenesulfonate salt of the cephalexin ester, p-nitrobenzyl 3-methyl-7-(D-2- amino-2-phenylacetamido)-3-cephem-4-carboxylate, 200 ml of N, N-dimethylformamide (DMF), and 20.0 ml of concentrated aqueous hydrochloric acid was stirred and kept at about 5° C. with external cooling while 10.4 g of powdered zinc was added portionwise during 0.5 hour. The mixture was then stirred for 1 hour without further cooling and kept at room temperature for several hours. After filtering, the cephalexin values in the filtrate were precipitated by gradually adjusting the apparent pH of the mixture to about 6.5 with triethylamine. The colorless, crystalline product, cephalexin bis-DMF solvate, was collected, washed with DMF and then with ethyl acetate, and dried. Product yield: 16.5 grams.

EXAMPLE 1

Cephalexin Hydrochloride Isopropanolate

A slurry of 284.4 g of cephalexin bis-DMF solvate (HPLC assay-69.4%) in 2.1 liters of isopropyl alcohol was cooled to 13° C. Concentrated hydrochloric acid (180 ml) was added rapidly, dropwise. During the acid addition the temperature of the slurry rose to 17° C., and the cephalexin bis-DMF solvate was dissolved. The resulting light yellow solution was warmed to about 20° C., seeded with several milligrams of cephalexin hydrochloride isopropanolate and stirred slowly at room temperature for about 2 hours during which time a thick slurry was produced. Hexane (1.38) was added to the stirred slurry over a period of about 15 minutes. The reaction mixture was then stirred for three hours at room temperature, cooled to about 15° C., and after about 45 minutes, the product, cephalexin hydrochloride isopropanolate, was filtered, washed with 2 100-ml portions of 1:1/isopropyl alcohol:hexane and dried in air overnight at room temperature. Yield: 245.4 grams (98.1% assay corrected yield).

Quantitative HPLC analysis

Theory: cephalexin, 78.3; isopropyl alcohol 13.5.
Found: cephalexin, 78.94; isopropyl alcohol, 12.96.
Elemental analysis calculated for $C_{16}H_{17}N_3O_4S \cdot HCl \cdot (CH_3)_2CHOH$.
Theory: Cl, 7.99.
Found: Cl, 8.28.

EXAMPLE 2

Cephalexin Hydrochloride Isopropanolate

The same procedure was followed as described in Example 1 above except that the reaction mixture was not seeded to promote crystallization of the crystalline isopropanol solvate. Additional isopropyl alcohol was required to facilitate stirring during solvate crystallization. Yield of air-dried product: 254.1 g, assay corrected yield (97.3%). HPLC analysis for cephalexin—79.22%.

EXAMPLE 3

Cephalexin Hydrochloride Isopropanolate

A solution of 47.4 g of cephalexin bis-DMF solvate (HPLC assay—63.39%) in 350 ml of isopropyl alcohol was cooled to 5° C. Concentrated hydrochloric acid (30 ml) was added drop-wise to the slurry. During the addition of hydrochloric acid the temperature of the slurry rose to about 13° C., and most of the cephalexin bis-DMF solvate went into solution. The solution was warmed to about room temperature and seeded with several milligrams of crystalline cephalexin hydrochloride isopropanolate. After stirring the resulting product slurry at room temperature for about 2 hours, hexanes (300 ml) was added over a 30-minute period. The resulting solution was stirred for an additional 2 hours at room temperature, cooled to about 15° C. and filtered. The product was washed with 100 ml of a mixture of equal volumes of isopropyl alcohol and hexanes and air dried to provide 34 grams of the titled product (assay corrected yield—89.8%).

EXAMPLE 4

Cephalexin Ethanolate - Desolvated Cephalexin Ethanolate

A slurry of 47.4 g of cephalexin bis-DMF solvate in 600 ml of 3A ethanol (K.F=0.03%) was stirred at room temperature and seeded with a few milligrams of a product from an earlier like preparation. After stirring the mixture 5 hours at room temperature, the ethanol in the mixture was evaporated until the total weight of the resulting slurry was 230 g. Filtration provided a crystalline cephalexin ethanol solvate. Air drying the product overnight, provided 35.1 g of crystalline desolvated cephalexin ethanolate.

EXAMPLE 5

Cephalexin Ethanolate - Desolvated Cephalexin Ethanolate

The same procedure was followed as in Example 4 above except that only 300 ml of 3A ethanol was used to form the reaction slurry. Nuclear magnetic resonance analysis of the air-dried product showed it to contain about 2.6 mole percent of dimethylformamide. The product was shown to contain 96.8 percent cephalexin by HPLC. The air-dried product was identified as desolvated cephalexin ethanolate.

EXAMPLE 6

Cephalexin Hydrochloride Ethanolate From Cephalexin Monohydrate

Cephalexin monohydrate (35.2 g) was suspended in 300 ml of 3A ethanol, and the resulting slurry was cooled to about 10° C. The slurry was stirred at that temperature while hydrogen chloride gas (9.2 g) was added to the mixture at a rate so as to maintain a temperature below about 23° C. All of the cephalexin monohydrate was dissolved after about the first 2½ minutes of the 5 minute HCl gas addition time. The resulting solution was seeded with a few milligrams of cephalexin hydrochloride ethanolate and stirred at room temperature for a total of 1½ hours during which time a thick slurry of a white crystalline product was produced. To the stirred slurry was added dropwise a mixture of hexanes (75 ml) and 3A ethanol (25 ml) over a 10 minute period. The reaction mixture was then stirred first at room temperature for about 1½ hours and then at about 3° C. for 2½ hours, after which time the reaction mixture was filtered to provide a white crystalline product. The product was washed with 2 10-ml portions of a 50:50 mixture of 3A ethanol/hexanes and finally with 20 ml of hexanes. After air drying for ¼ hour the product weighed 36.3 grams. Air drying was continued overnight at about 30° C. Analysis of the dried product (35.2 g) was as follows: Cephalexin (HPLC), 85.67%; Ethanol (NMR), 45 mole %; and water (K.F.), 2.56%.

The analysis of the product after air drying overnight indicated that the conversion of the original product, cephalexin hydrochloride ethanolate, to cephalexin hydrochloride monohydrate was only partially complete. The product was exposed to air at ambient temperature and humidity for an additional 5 days and bottled. Product weight: 33.79 grams (Assay corrected yield: 87.2%).

Analysis for cephalexin hydrochloride monohydrate:

Theory: cephalexin, 86.4; ethanol, 0; chloride, 9.1; water, 4.5.

Found: cephalexin (HPLC), 85.71; ethanol, 0.41; chloride, 8.84; water (K.F.), 5.12.

EXAMPLE 7

Cephalexin Hydrochloride Ethanolate Via Cephalexin Monohydrate

The same experimental procedure was followed as in Example 6 above, except that 100 ml of hexanes was added to the product slurry instead of a mixture of 75 ml hexanes and 25 ml 3A ethanol. Yield of cephalexin hydrochloride ethanolate: 38.2 g (93%). After drying the product overnight in air at about 30° C. the crystalline product (37.1 g) was analyzed as follows:

Cephalexin (HPLC), 85.09; ethanol (NMR), 45 mole percent; water (K.F.), 2.29.

After drying the product in air at room temperature for about 5 days the product (30.32 g, 91.3% assay corrected yield) was analyzed as follows:

Theory: cephalexin, 86.4; ethanol, 0.0; water, 4.5; chloride, 9.1.

Found: cephalexin (HPLC), 85.18; ethanol, 0.38; water (K.F.), 5.02; chloride, 8.94.

EXAMPLE 8

Cephalexin Hydrochloride Ethanolate Via Cephalexin Monohydrate

The same procedure was followed as in Example 6 above except that the volume of 3A ethanol (K.F.=0.02 percent) was 100 ml instead of 144 ml and 70 ml of pentane was used in place of the mixture of hexanes and ethanol. Filtration of the product slurry provided, after washing, 36 g of cephalexin hydrochloride ethanolate. Air drying provided 34.2 g of cephalexin hydrochloride monohydrate (88.6% assay corrected yield).

EXAMPLE 9

Cephalexin Hydrochloride Ethanolate From Cephalexin Monohydrate

Cephalexin monohydrate (35.2 g) was added to a solution of 7.1 g of gaseous hydrogen chloride in 100 ml of 3A ethanol (K.F. =0.03 percent) at about 16° C. The addition of cephalexin monohydrate caused the temperature of the reaction mixture to rise to about 24° C.; the cephalexin monohydrate dissolved. The solution was then seeded and stirred at room temperature for about 1 hour. Hexanes (100 ml) were added to the mixture. The slurry separated into two phases. The mixture was stirred for ½ hour at room temperature and thereafter 2½ hours at about 5° C. before being filtered to provide a white crystalline product which was washed with 2 25-ml portions of a mixture of equal volumes of 3A ethanol and hexanes and finally with 25 ml hexanes to provide white crystalline cephalexin hydrochloride ethanolate (38 g). The product reached a constant weight (35.8 g) after air drying at room temperature for about 1 week indicating completion of the conversion of the ethanol solvate to the monohydrate. HPLC analysis—86.76% cephalexin (93.6% assay corrected yield).

EXAMPLE 10

Cephalexin Hydrochloride Ethanolate Via Cephalexin Monohydrate

The same procecedure was followed as described in Example 9 above except that 140 ml of 2B ethanol (K.F.=0.05%) was substituted for the 100 ml of 3A ethanol. The procedure provided 38.2 g of crystalline cephalexin hydrochloride ethanolate which was air dried over 1 week to form 36.6 g of cephalexin hydrochloride monohydrate (96% assay corrected yield).

EXAMPLE 11

Cephalexin Hydrochloride Ethanolate Via Cephalexin Monohydrate

The same procedure was followed as in Example 9 above except that 144 ml of punctilious ethanol denatured with hexanes (2.5 ml hexanes/500 ml ethanol—K.F. 0.03 percent) was substituted for the 3A ethanol and only 6.2 g of gaseous HCl was used to form the solution of cephalexin hydrochloride. The procedure provided 39.0 g of cephalexin hydrochloride ethanolate which was air dried for about 10 days to provide 37.0 g of cephalexin hydrochloride monohydrate (96.4 percent assay corrected yield by HPLC analysis).

Repeating that procedure using 105.6 g of cephalexin monohydrate and 19.0 g of gaseous hydrogen chloride in 432 ml of punctilious ethanol (K.F.=0.00 percent) provided 113.6 g of cephalexin hydrochloride ethanolate air drying over a period of about 1 week provided 110.6 g of cephalexin monohydrate hydrochloride as a crystalline white solid (96.5% assay corrected yield).

EXAMPLE 12

Cephalexin Hydrochloride Ethanolate Via Desolvated Cephalexin Ethanolate

Desolvated cephalexin ethanolate (30 g, HPLC assay - 95.33%), obtained via the cephalexin ethanolate from cephalexin bis-DMF solvate, was slurried in 120 ml ethanol (K.F. 0.03 percent) and treated with 7 g of gaseous hydrogen chloride while maintaining the reaction mixture temperature less than 25° C. After stirring the mixture for 1 hour at room temperature, 80 ml of hexanes was added over 15 minutes to the stirred mixture. The stirring of the reaction mixture was continued for 1 hour at room temperature and thereafter for 4 hours at about 15° C. The crystalline cephalexin hydrochloride ethanolate product was filtered, washed with a mixture of equal volumes of ethanol and hexanes, and finally with hexanes, and then air dried at 28° C. to provide 30.6 g of crystalline cephalexin hydrochloride ethanolate. Air drying for about 1 week at room temperature provided cephalexin monohydrate hydrochloride (29.5 g, 89.4% assay corrected yield).

The foregoing procedure was repeated using 34.8 g desolvated cephalexin ethanolate, 8 g gaseous hydrogen chloride, 125 ml 2B ethanol (K.F. 0.03 percent) and 80 ml hexanes. Filtration of the final reaction mixture provided 35.4 g of cephalexin hydrochloride ethanolate which was air dried over a 1 week period at room temperature to provide cephalexin hydrochloride monohydrate (33.8 g, 88.9% assay corrected yield).

EXAMPLE 13

Cephalexin Hydrochloride Methanolate Via Cephalexin Monohydrate

Methanol (200 ml, K.F.=0.12 percent) was treated with 15.1 g of gaseous HCl at room temperature. Cephalexin monohydrate (70.4 g) was added, and it immediately dissolved in the methanolic-HCl mixture. While stirring the mixture for about 20 minutes at room temperature, a thick slurry formed. Pentane (100 ml) was added over a 5 minute period to the stirred mixture. The mixture was then cooled to about 5° C. and stirred for 6 hours. The crystalline product was filtered, washed with 100 ml of an equal volume mixture of methanol and pentane, and finally with 100 ml pentane to provide cephalexin hydrochloride methanolate as an off-white crystalline solid. The conversion of cephalexin hydrochloride methanolate to cephalexin hydrochloride monohydrate (by exposure to moist air) appeared to occur much more rapidly than that with cephalexin hydrochloride ethanolate. After drying the product overnight at 28° C. the product (63.5 g) gave the following analysis:

Cephalexin (HPLC), 84.95%; water (K.F.), 4.10% and methanol, 0.9%.

Assay corrected yield of cephalexin monohydrate hydrochloride—81.3%.

EXAMPLE 14

Cephalexin Hydrochloride Ethanolate Via Cephalexin Hydrochloride Isopropanolate Cephalexin hydrochloride isopropanolate (38.0 g - HPLC assay 80.35%) was slurried in dry (K.F. 0.03%) 3A ethanol at room temperature for 3 hours. Hexanes (100 ml) were added over a 10 minute period and the resultant thick stirred slurry was cooled to about 5° C. for 1 hour and filtered. The product was washed first with 250 ml portions of a mixture of equal volumes of hexanes and 3A ethanol and finally with 50 ml hexanes, and air dried to provide 32 g of cephalexin hydrochloride ethanolate. Air drying that product at room temperature for about 1 week provided 29.3 g (82.5% assay corrected yield) of cephalexin monohydrate hydrochloride which analyzed as follows:

Cephalexin (HPLC), 85.9%; ethanol, 0.08%; water (K.F.), 4.96%.

EXAMPLE 15

Cephalexin Hydrochloride Ethanolate Via Cephalexin Hydrochloride Isopropanolate Cephalexin hydrochloride isopropanolate (43 g) was slurried in 140 ml of dry (K.F. 0.02 percent) 3A ethanol, and the resulting slurry was warmed to about 47° C. for 6 hours and then cooled to room temperature. The slurry was then treated with 200 ml hexanes, stirred at room temperature for 1 hour, cooled to 4° C. and after 1 hour, filtered to provide crystalline product. The product was washed with 2 50-ml portions of a mixture of equal volumes of ethanol and hexanes and then with 50 ml hexanes. Air drying the product for about 2 weeks provided 35.4 g cephalexin hydrochloride monohydrate (89.0% assay corrected yield). Product analysis:

Cephalexin (HPLC), 85.68%; water (K.F.), 4.61%; ethanol, 0.37%; isopropanol, 0.02%.

The procedure in the foregoing paragraph was repeated except that the slurry of cephalexin hydrochloride isopropanolate in 3A ethanol was stirred at room temperature for 20 hours (overnight). The procedure provided initially 38.2 g of cephalexin hydrochloride ethanolate which was air dried over a 2 week period to provide 36.2 g (88.7% assay corrected yield) of cephalexin hydrochloride monohydrate.

I claim:

1. In a method for the preparation of crystalline cephalexin hydrochloride ethanol solvate (ethanolate) or methanol solvate (methanolate) by forming a solution of cephalexin hydrochloride in ethanol or methanol, respectively, and crystallizing the respective solvate, the improvement which comprises
   (1) forming a solution of cephalexin hydrochloride in a volume of substantially anhydrous ethanol or methanol, respectively;
   (2) initiating crystallization of the cephalexin hydrochloride solvate, if necessary;
   (3) adding to the ethanolic or methanolic solution of cephalexin hydrochloride up to an equivalent volume of an alkane selected from $C_5$-$C_6$ alkanes and $C_5$-$C_6$ cycloalkanes to form a crystal-forming medium; and
   (4) separating the crystalline cephalexin hydrochloride solvate from the crystal-forming medium.

2. The improved method of claim 1 wherein crystalline cephalexin hydrochloride methanolate is separated from a crystal-forming medium formed by adding hexanes or pentanes to a solution of cephalexin hydrochloride in substantially anhydrous methanol.

3. The improved method of claim 2 wherein the methanol contains less than about 1.0% water by the Karl Fischer method of analysis.

4. The improved method of claim 2 wherein the solution of cephalexin hydrochloride has a concentration of about 0.2 to about 1.0 grams of cephalexin hydrochloride per milliliter of methanol.

5. The improved method of claim 4 wherein the alkane is pentane or hexanes and the volume of pentane or hexanes added to the alcoholic solution of cephalexin hydrochloride is about 20 to about 50% of the total volume of the crystal-forming medium.

6. The improved method of claim 5 wherein the methanol contains less then 1.0% water by the Karl Fischer method of analysis.

7. The improved method of claim 5 wherein the solution of cephalexin hydrochloride in methanol is formed by adding at least a molar equivalent amount of gaseous HCl to a solution or slurry of cephalexin monohydrate, cephalexin ethanolate, or cephalexin anhydrate in substantially anhydrous methanol.

8. The improved method of claim 7 wherein the volume of pentane or hexanes added to the methanolic solution of cephalexin hydrochloride is about 40% of the total volume of the crystal-forming medium.

9. The improved method of claim 5 wherein the solution of cephalexin hydrochloride is formed by adding cephalexin hydrochloride isopropanolate to a volume of substantially anhydrous methanol.

10. The improved method of claim 9 wherein the volume of hexanes added to the alcoholic solution of cephalexin hydrochloride is about 40% of the total volume of the crystal-forming medium.

11. The improved method of claim 1 wherein crystalline cephalexin hydrochloride ethanolate is separated from a crystal-forming medium formed by adding hexanes or pentane to a solution of cephalexin hydrochloride in substantially anhydrous ethanol.

12. The improved method of claim 11 wherein the substantially anhydrous ethanol contains less than 0.2% water by the Karl Fischer method of analysis.

13. The improved method of claim 11 wherein the solution of cephalexin hydrochloride has a concentration of about 0.2 to about 1.0 grams of cephalexin hydrochloride per milliliter of ethanol.

14. The improved method of claim 13 wherein the lower alkanes are hexanes and the volume of hexanes added to the alcoholic solution of cephalexin hydrochloride is about 20 to about 50% of the total volume of the crystal-forming medium.

15. The improved method of claim 14 wherein the substantially anhydrous ethanol contains less than about 0.05% water by the Karl Fischer method of analysis.

16. The improved method of claim 14 wherein the solution of cephalexin hydrochloride in ethanol is formed by adding at least a molar equivalent amount of gaseous HCl to a solution or slurry of cephalexin monohydrate, cephalexin ethanolate, or a cephalexin anhydrate, in substantially anhydrous ethanol.

17. The improved method of claim 16 wherein the volume of hexanes added to the ethanolic solution of cephalexin hydrochloride is about 40% of the crystal-forming medium.

18. The improved method of claim 14 wherein the solution of cephalexin hydrochloride in ethanol is formed by adding cephalexin hydrochloride isopropanolate to substantially anhydrous ethanol.

19. The improved method of claim 18 wherein the volume of hexanes added to the ethanolic solution of cephalexin hydrochloride is about 40% of the volume of the crystal-forming medium.

20. In a method for preparing crystalline cephalexin hydrochloride isopropanolate by crystallizing said isopropanolate from a solution of cephalexin hydrochloride in isopropanol, the improvement which comprises preparing the solution of cephalexin hydrochloride by forming a slurry of cephalexin bis-dimethylformamide solvate in about 5 to about 15 ml of isopropanol per gram of the bis-dimethylformamide solvate; adding at least an equivalent amount of HCl in the form of concentrated hydrochloric acid, or its equivalent in the form of gaseous HCl and water, to the slurry to form a crystal-forming medium; and separating the crystalline cephalexin hydrochloride isopropanolate from the crystal-forming medium.

21. The improved method of claim 20 wherein following the addition of the hydrochloric acid the crystal-forming medium is seeded with crystals of cephalexin hydrochloride isopropanolate.

22. The improved method of claim 21 wherein a volume of $C_5$–$C_6$ alkanes or $C_5$–$C_6$ cycloalkanes is added to the crystal-forming medium, the volume of said alkanes equalling about 20 to about 50% of the total volume of the crystal-forming medium.

23. The improved method of claim 22 wherein the slurry of the bis-dimethylformamide solvate of cephalexin in isopropanol is cooled to about 0° to about 15° C. prior to the addition of hydrochloric acid.

24. A method for the preparation of cephalexin in crystalline form, which method comprises
(1) forming a slurry of cephalexin bis-dimethylformamide solvate in substantially anhydrous ethanol;
(2) seeding the slurry with crystals of cephalexin ethanolate or desolvated cephalexin ethanolate and stirring the slurry at room temperature for about 30 minutes to about 12 hours;
(3) separating the product crystalline cephalexin ethanolate from the resulting slurry; and
(4) drying the product cephalexin ethanolate to provide crystalline desolvated cephalexin ethanolate.

25. The method of claim 24 wherein the ethanol contains less than about 0.2% water by the Karl Fischer method of analysis.

26. The method of claim 24 wherein the ethanol contains less than about 0.05% water by the Karl Fischer method of analysis.

27. Cephalexin ethanolate.

* * * * *

UNITED STATES PATENT AND TRADEMARK OFFICE
CERTIFICATE OF CORRECTION

PATENT NO.   :   4,775,751

DATED        :   October 4, 1988

INVENTOR(S)  :   Lawrence J. McShane et al.

It is certified that error appears in the above-identified patent and that said Letters Patent is hereby corrected as shown below:

On the bibliography page at [75] Inventor:, please add --and Gary L. Engel, Greenwood, Ind.--.

Signed and Sealed this

Twelfth Day of September, 1989

Attest:

DONALD J. QUIGG

Attesting Officer

Commissioner of Patents and Trademarks